United States Patent [19]

Bene et al.

[11] Patent Number: 5,725,775
[45] Date of Patent: *Mar. 10, 1998

[54] ARTIFICIAL KIDNEY DOSING METHOD

[75] Inventors: Bernard Bene, Irigny; Jacques Chevallet, Serezin Du Rhone, both of France

[73] Assignee: Hospal Industrie, France

[*] Notice: The term of this patent shall not extend beyond the expiration date of Pat. No. 5,578,223.

[21] Appl. No.: 493,969

[22] Filed: Jun. 23, 1995

Related U.S. Application Data

[62] Division of Ser. No. 383,208, Feb. 3, 1995, Pat. No. 5,578,223, which is a division of Ser. No. 942,466, Sep. 9, 1992, abandoned.

[30] Foreign Application Priority Data

Sep. 10, 1991 [FR] France ................... 91 11351

[51] Int. Cl.$^6$ .................. B01D 61/22; B01D 61/32; A61M 1/14; A61M 1/34
[52] U.S. Cl. .................. 210/646; 210/645; 210/650; 210/739; 210/929; 604/4; 604/5
[58] Field of Search .................. 210/645, 646, 210/650, 739, 929, 85, 87, 97, 103, 134, 143, 195.2, 257.2, 258, 321.6, 321.65, 321.71, 321.72, 321.75, 321.84; 604/4, 5, 6, 28, 65, 66, 67

[56] References Cited

U.S. PATENT DOCUMENTS

| 4,132,644 | 1/1979 | Kolberg | 210/85 |
|---|---|---|---|
| 4,178,240 | 12/1979 | Pinkerton | 417/393 |
| 4,204,957 | 5/1980 | Weickhardt | 210/98 |
| 4,324,663 | 4/1982 | Hirel et al. | 210/646 |
| 4,372,846 | 2/1983 | Yamagami et al. | 210/86 |
| 4,582,598 | 4/1986 | Bilstad et al. | 210/101 |
| 4,606,826 | 8/1986 | Sano et al. | 210/646 |

(List continued on next page.)

FOREIGN PATENT DOCUMENTS

| 0 192 588 | 8/1986 | European Pat. Off. |
|---|---|---|
| 0 256 956 | 2/1988 | European Pat. Off. |
| 0 321 754 | 6/1989 | European Pat. Off. |
| 0 373 455 | 6/1990 | European Pat. Off. |
| 2 332 031 | 6/1977 | France . |
| 2 397 197 | 2/1979 | France . |
| 27 03 188 | 8/1978 | Germany . |

OTHER PUBLICATIONS

"Buffer Balance in Bicarbonate Hemodiafiltration," by M. Feriani et al., A.S.A.I.O., vol. 32, No. 1, pp. 422–424, Jul.–Sep. 1986.

Lewis, "Arteriovenous Hemofiltration with Dialysis," Critical Care Report 1990:1:408–414.

Sartorius, Haemoprocessor, 400 20, Operating Instructions (1984).

Gambro, Hemofiltration, Operator's manual for hemofiltration BMM 10–1, FHM 10–1 (1986).

*Primary Examiner*—John Kim
*Attorney, Agent, or Firm*—Finnegan, Henderson, Farabow, Garrett & Dunner L.L.P.

[57] ABSTRACT

An artificial kidney dosing method includes the steps of connecting a patient to an exchanger having first and second compartments separated by a semipermeable membrane. The first compartment is connected to a circuit for extracorporeal blood circulation, and the second compartment has an outlet for draining a waste liquid. After the patient is connected to the exchanger, a perfusion liquid containing a substance (A) is perfused to the patient. The concentration of substance (A) in the blood of the patient is adjusted to a desired concentration $\{A\}_{DES}$, by controlling a flow rate $(Q_A)$ of the perfusion liquid as a function of (1) a flow rate $(Q_{OUT})$ of the waste liquid; (2) the desired concentration $\{A\}_{DES}$; and (3) a concentration $\{A\}_{SOL}$ of substance (A) in the perfusion liquid, whereby during this adjustment, a transfer of substance $\{A\}$ through the semipermeable membrane is taken into account.

21 Claims, 2 Drawing Sheets

U.S. PATENT DOCUMENTS

| Patent No. | Date | Inventor | Class |
|---|---|---|---|
| 4,684,460 | 8/1987 | Issautier | 210/90 |
| 4,711,715 | 12/1987 | Polaschegg | 210/103 |
| 4,728,433 | 3/1988 | Buck et al. | 210/646 |
| 4,759,132 | 7/1988 | Patono | 210/86 |
| 4,767,399 | 8/1988 | Bollish | 210/646 |
| 4,844,810 | 7/1989 | Richalley et al. | 210/646 |
| 4,889,635 | 12/1989 | Chevallet | 210/646 |
| 4,923,598 | 5/1990 | Schal | 210/87 |
| 4,980,054 | 12/1990 | Lavender | 210/90 |
| 5,047,147 | 9/1991 | Chevallet et al. | 210/101 |
| 5,100,554 | 3/1992 | Polaschegg | 210/647 |
| 5,178,763 | 1/1993 | Delaunay | 210/646 |
| 5,211,849 | 5/1993 | Kitaevich et al. | 210/645 |
| 5,366,630 | 11/1994 | Chevallet | 210/646 |
| 5,401,238 | 3/1995 | Pirazzoli | 604/4 |

ARTIFICIAL KIDNEY DOSING METHOD

This is a division of application Ser. No. 08/383,208, filed Feb. 3, 1995, now U.S. Pat. No. 5,578,223, which is a divisional of application Ser. No. 07/942,466 filed Sep. 9, 1992, abandoned.

The present invention relates to an artificial kidney enabling substances to be dosed into the blood and which is also particularly adapted to treating people suffering temporarily from kidney failure following an accident or a surgical operation.

The substances concerned may, for example, be medicines (in particular antibiotics), glucose, or certain blood electrololytes (potassium, magnesium, and bicarbonate, in particular). The invention is described below in its application to dosing bicarbonate, but it will be understood that this particular example is given purely by way of illustration and is not limiting in any way.

It is known that in addition to purifying plasma wastes (urea, creatinine) and to excreting water, the kidneys play an important part in maintaining the acid-base equilibrium of the internal medium, in particular by eliminating weak acids (phosphates, monosodium acids) and by producing ammonium salts.

In people who have lost their kidney function either temporarily or permanently, because this regulating mechanism is no longer operating, an increase is observed in the acidity of the internal medium (acidosis), i.e. a drop in the pH of the blood serum towards 7 (where blood pH normally lies within the very narrow limits of 7.35 to 7.45).

The conventional way of mitigating this deficiency of the regulating mechanism of the kidneys is to act on another mechanism for regulating the acid-base equilibrium of the internal medium, which mechanism is constituted by buffer systems of the blood, and the main such system comprises carbonic acid as a weak acid in association with its alkaline salt, bicarbonate. Thus, to combat the acidosis of a person suffering from kidney failure, bicarbonate is caused to pass into the blood, generally simultaneously with a session during which the blood is purified by hemofiltration or by hemodialysis.

During treatment by hemofiltration, where blood is purified by ultrafiltration of plasma water through a semipermeable membrane accompanied by convective transfer of plasma wastes, bicarbonate is added by perfusing a solution of sodium bicarbonate.

During hemodialysis treatment where blood is purified by plasma wastes being transferred by diffusion through a semipermeable membrane with blood being circulated on one face of the membrane and a dialysis liquid being circulated on the other face, bicarbonate may be added in two ways, depending on whether the dialysis liquid contains bicarbonate or whether it has none.

When the dialysis liquid contains bicarbonate, then bicarbonate is added to the blood by diffusion from the dialysis liquid through the semipermeable membrane into the blood, and the bicarbonate concentration in the dialysis liquid is adjusted accordingly.

When the dialysis liquid does not contain bicarbonate, then a solution of sodium bicarbonate is perfused into the patient as during hemofiltration treatment, and in sufficient quantity to compensate for the diffusive losses (or the convective losses in hemofiltration) that occur in the membrane exchanger and to compensate for the deficit from which the patient in an acidotic state is suffering.

The final concentration of bicarbonate in the blood of a patient subjected to either of these treatments depends on the concentration of bicarbonate in the perfusion solution or in the dialysis liquid, on the respective flow rates thereof, and on the flow rate of the patient's blood through the membrane exchanger. With the exception of the concentration of the sodium bicarbonate solution which is fixed by the manufacturer, these parameters are, at present, determined empirically by the doctor on the basis of blood pH measurements that are performed regularly for such patients in a state of shock, whose blood is being dialyzed or ultrafiltered on a permanent basis, or as performed after one treatment session and before the following session for patients who have lost kidney function permanently. It results therefrom that the concentration of bicarbonate in the blood of the patient corresponds rarely exactly to the desired concentration.

An object of the invention is to provide an artificial kidney which enables the acide-base equilibrium of a patient being subjected to renal purification treatment to be adjusted accurately.

According to the invention, this object is achieved by an artificial kidney comprising:

an exchanger having two compartments separated by a semipermeable membrane, a first compartment being connected to a circuit for extracorporeal blood circulation connectable to a patient, a second compartment having an outlet for draining a waste liquid, means for perfusing to the patient a perfusion liquid containing a substance (A), and dosage means for adjusting the concentration of substance (A) in the blood of the patient to a desired concentration $[A]_{DES}$, whereby a transfer of substance (A) through the semipermeable membrane is taken into account.

According to a characteristic of the invention, the dosage means comprise means for controlling a flow rate $Q_A$ of the perfusion liquid as a function of a flow rate $Q_{OUT}$ of the waste liquid.

According to another characteristic of the invention, the flow rate $Q_A$ of the perfusion liquid and the flow rate $Q_{OUT}$ of the waste liquid are related by the equation:

$$Q_A = \frac{[A]_{DES}}{[A]_{SOL}} \times Q_{OUT}$$

or by the equation:

$$Q_A = \frac{[A]_{DES}}{[A]_{SOL}} \times Cl$$

where $[A]_{SOL}$ is the concentration of the substance (A) in the sterile solution and Cl is the clearance of the artificial kidney for the substance (A).

According to another characteristic of the invention, the substance (A) being bicarbonate, the artificial kidney includes a source of substitution/dialysis liquid that does not contain bicarbonate connected to the circuit for extracorporeal blood circulation and to an inlet of the second compartment of the exchanger, and blocking means for either isolating the source or enabling the substitution/dialysis liquid to flow out into the circuit for extracorporeal blood circulation, or else for allowing the substitution/dialysis liquid to flow into the second compartment of the exchanger.

According to yet another characteristic of the invention, the artificial kidney includes means for measuring the difference between the flow of liquid(s) injected into the circuit for extracorporeal blood circulation and the flow of waste liquid (ultrafiltrate and/or waste dialysis liquid) flowing out from the second compartment of the exchanger. The means for measuring the difference between the liquid flows may comprise scales for weighing a container constituting a source of substitution/dialysis liquid and a container for collecting waste liquid, and scales for weighing a container constituting a source of solution containing the substance.

The object of the invention is also achieved by a method for dosing a substance (A) in the blood of a patient connected to an artificial kidney comprising an exchanger having two compartments separated by a semipermeable membrane, a compartment having an outlet for draining a waste liquid, the method comprising the steps of:

perfusing into the patient a liquid containing the substance (A), and controlling a flow rate $Q_A$ of the perfusion liquid as a function of a flow rate $Q_{OUT}$ of the waste liquid.

Other characteristics and advantages of the invention appear on reading the following description. Reference is made to the accompanying drawings, in which.

Figure 1:
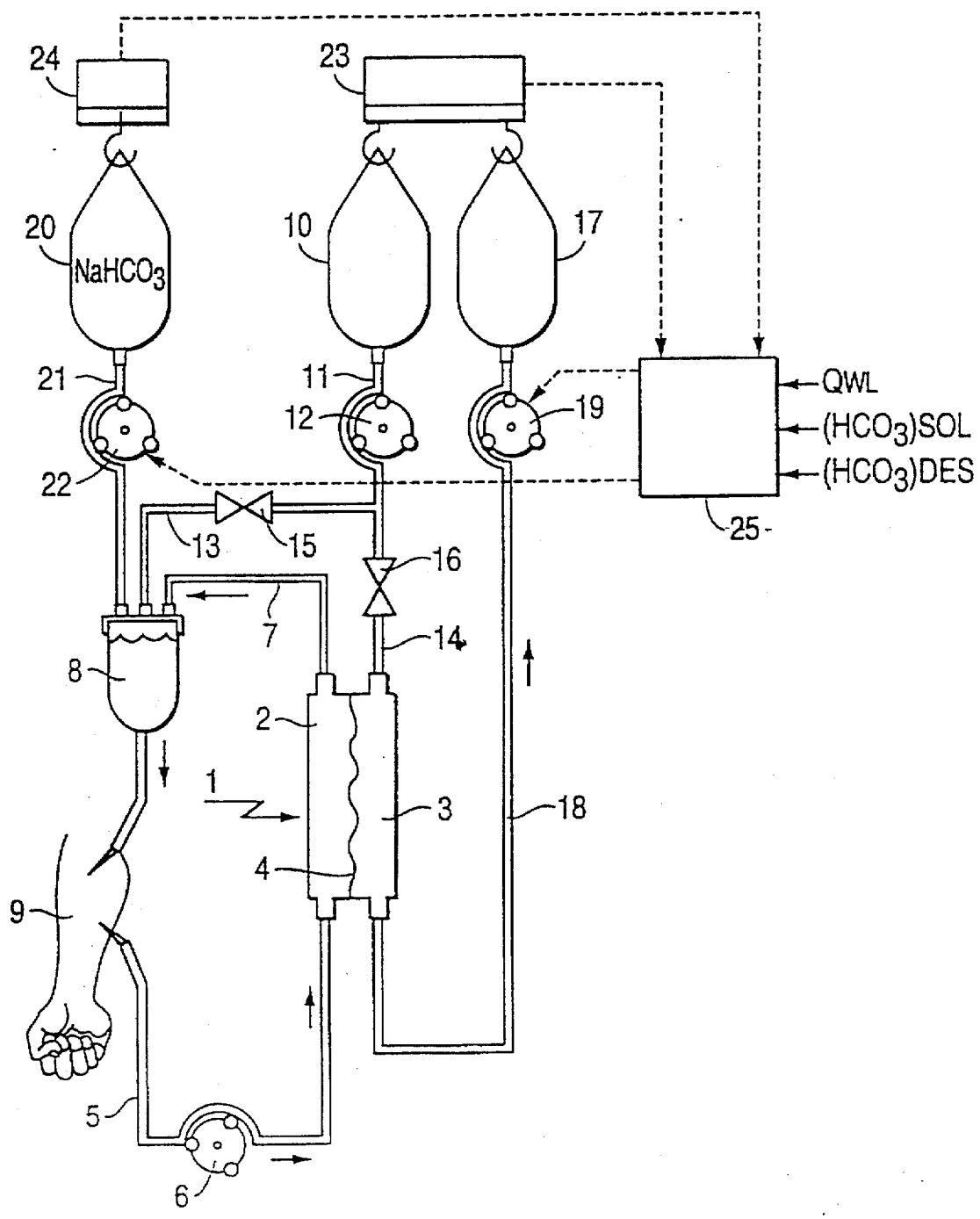
FIG. 1 is a simplified diagram of a first embodiment of the invention.

The artificial kidney shown in FIG. 1 comprises an exchanger 1 having two compartments 2 and 3 separated by a semipermeable membrane 4. The compartment 2 is connected to a circuit for extracorporeal blood circulation and comprising an upstream duct 5 having a circulation pump 6 disposed thereon, and a downstream duct 7 fitted with a bubble trap 8. The ducts 5 and 7 have their free ends provided with respective needles or catheter connectors for connecting the circuit for extracorporeal blood circulation outside the body to the vascular system of a patient 9.

A container 10 containing sterile substitution/dialysis liquid that does not contain any bicarbonate is connected via common length of duct 11 which has a circulation pump 12 disposed thereon to two ducts 13 and 14 that are connected respectively to the bubble trap 8 and to an inlet of the second compartment 3 of the exchanger 1. Blocking means 15 and 16 such as electromagnetically-operated clamps are provided on the ducts 13 and 14 respectively to enable the container 10 to be isolated or connected selectively to the exchanger 1 or to the circuit for extracorporeal blood circulation.

A second container 17 for waste liquid (ultrafiltrate and/or waste dialysis liquid) is connected to an outlet of the second compartment 3 of the exchanger 1 by a duct 18 which has an extraction pump 19 for the waste liquid disposed thereon. The pump 19 serves to establish a variable pressure drop in the compartment 3 of the exchanger 1, i.e. it serves to vary the transmembrane pressure and consequently the ultrafiltration flow rate.

A third container 20 containing a sterile solution of sodium bicarbonate is connected to the bubble trap 8 by means of a duct 21 which has a circulation pump 22 disposed thereon.

In accordance with the invention, the artificial kidney shown in FIG. 1 includes means for measuring the difference between the liquid(s) perfused into the patient 9 and the waste liquid, optionally for determining a desired weight loss to be achieved by extracting a quantity of plasma water that is greater than the quantity of perfused liquid(s), and to establish a determined value of bicarbonate concentration in the plasma of the patient. These means comprise first scales 23 for weighing the container 10 of substitution/dialysis liquid and the container 17 of waste liquid, second scales 24 for weighing the container 20 of sodium bicarbonate solution, and a control unit 25 suitable for receiving the data delivered by the scales 23 and 24 as input signals, a reference value $Q_{WL}$ for the desired weight loss flow rate, the value $[HCO_3]_{SOL}$ of the concentration of bicarbonate in the solution contained in the container 20, and a reference value $[HCO_3]_{DES}$ for the desired concentration of bicarbonate in the blood. The control unit 25 is designed to control the waste liquid extraction pump 19 taking into account the desired weight loss flow rate $Q_{WL}$ and the flow rate $Q_{IN}$ imposed to the pump 12 for circulating the substitution/ dialysis liquid, and to control the pump 22 for perfusing the bicarbonate solution taking into account the flow rate $Q_{OUT}$ of the waste liquid extraction pump 19.

In accordance with the invention, the flow rate $Q_{HCO3}$ of the perfusion pump 22 can be controlled as a function of the flow rate $Q_{OUT}$ of the extraction pump 19 regardless of the type of treatment being delivered to the patient (hemofiltration with or without perfusion of substitution liquid, hemodialysis, or hemodiafiltration) by the equation:

$$Q_{HCO3} = Q_{OUT} \times \frac{[HCO_3]_{DES}}{[HCO_3]_{SOL}} \tag{1}$$

The above-described artificial kidney operates as follows: In homofiltration mode without any substitution liquid being perfused, the clamps 15 and 16 are closed, the pump 12 for circulating the substitution/dialysis liquid is off, and the pumps 19 and 22 for extracting the blood filtrate and the perfusion of bicarbonate solution are on. The control unit 25 continuously adjusts the flow rate $Q_{OUT}$ of the extraction pump 19 as measured by means of the scales 23 so that the flow rate is permanently equal to the sum of the desired weight loss flow rate $Q_{WL}$ and the flow rate $Q_{HCO3}$ of the perfusion of bicarbonate solution as measured by means of the scales 24. The control unit 25 also continuously adjusts the flow rate $Q_{HCO3}$ of the pump 22 for perfusing the bicarbonate solution as a function of the desired concentration of bicarbonate $[HCO_3]_{DES}$ in the blood of the patient, of the concentration $[HCO_3]_{SOL}$ of the solution contained in the container 20 and of the convective losses that occur in the exchanger 1, which losses are equal to $Q_{OUT} \times [HCO_3]_{BLD}$, where $[HCO_3]_{BLD}$ is the concentration of bicarbonate in the blood of the patient, and where the transmittance of the high permeability membranes used for homofiltration is equal to 1 for blood electrolytes (recall that the general formula giving the mass flow rate Js of a substance passing through a membrane as a function of the volume flow rate Jv of plasma water is the following:

$$Js = Jv \times Tr \times Cs$$

where Cs is the concentration of the substance in the blood and where Tr is the transmittance of the membrane relative to said substance).

The pump 22 for perfusing the bicarbonate solution being servo-controlled in compliance with equation (1) given above enables thus the blood of the patient 9 to be brought progressively to an equilibrium state where its concentration of bicarbonate is equal to $[HCO_3]_{DES}$.

In hemofiltration mode with perfusion of substitution liquid, the clamp 16 is closed, the clamp 15 is open and all three pumps 12, 19, and 22 are on, with the flow rate of the pump 12 being fixed by the operator to a constant value at the beginning of a treatment session. The operation of the artificial kidney in this second treatment mode differs from that described above only in that to control the extraction pump 19 the control unit 25 takes account of the emptying of the container 10, with the flow rate $Q_{OUT}$ imposed on the pump 19 then being selected so that the difference between the flow rate of substitution liquid and the flow rate of waste liquid as measured by the scale 23 is equal to the sum of the desired weight loss flow rate $Q_{WL}$ and the perfusion rate $Q_{HCO3}$ of bicarbonate solution as measured by the scales 24. The perfusion pump 22 for the bicarbonate solution is adjusted as before in compliance with the servo-control specified by equation (1).

In hemodialysis mode, the clamp 15 is closed, the clamp 16 is open, and all three pumps 12, 19 and 22 are on. The control unit 25 continuously adjusts the flow rate $Q_{OUT}$ of the extraction pump 19 so that the difference between the flow rate of dialysis liquid and the flow rate of waste liquid as measured by the scales 23 is continuously equal to the perfusion flow rate $Q_{HCO3}$ of bicarbonate solution as measured by the scales 24, with the weight loss flow rate reference value being zero.

The control unit 25 also controls the perfusion flow rate $Q_{HCO3}$ of the bicarbonate solution as a function of the desired bicarbonate concentration $[HCO_3]_{DES}$ for the blood of the patient, of the concentration $[HCO_3]_{SOL}$ of the solution contained in the container 20, and of the diffusive loss through the exchanger 1 which is given by $Cl \times [HCO_3]_{BLD}$, where $[HCO_3]_{BLD}$ is the concentration of bicarbonate in the blood of the patient and where Cl is the clearance of the artificial kidney for bicarbonate (the "clearance" is defined in general terms as the ratio between the quantity of substance eliminated per unit time and the concentration of the substance in the blood at the inlet of the exchanger.) To ensure that the concentration of bicarbonate in the blood reaches a given value $[HCO_3]_{DES}$ at equilibrium, it is therefore necessary to control the perfusion flow rate $Q_{HCO3}$ of the pump 22 for the bicarbonate solution in compliance with the equation:

$$Q_{HCO3} = Cl \times \frac{[HCO_3]_{DES}}{[HCO_3]_{SOL}} \quad (2)$$

which assumes that the clearance of the artificial kidney has previously been determined, which clearance depends on the type of exchanger used (nature of the membrane, area) and, in general, on the flow rates of blood and of dialysis liquid through the exchanger.

However, for certain values of blood flow rate and of dialysis liquid flow rate, the clearance of the kidney for a given substance and a given type of exchanger is substantially constant. This applies in particular when first the area of the membrane in the exchanger is sufficiently large relative to the blood flow rate and second the blood flow rate is relatively large compared with the dialysis liquid flow rate (being about three or more times said rate). Under such circumstances, the blood and the dialysis liquid leaving the exchanger have the same concentration of the substance under consideration and the clearance Cl is equal to the outlet flow rate of the waste liquid $Q_{OUT}$. In other words, under these particular operating conditions, the control of the pump 22 for perfusing the bicarbonate solution is defined by equation (1). These conditions are applicable to continuous dialysis treatment of patients in a state of shock for whom purification must be performed at a moderate rate so that their weakened organism can tolerate it.

The artificial kidney of the invention thus has a particular advantage for treating patients who have temporarily lost kidney function since, whatever the type of treatment to which they are subjected, this artificial kidney makes it possible to act on their acid-base equilibrium in a manner that is simple by controlling one pump only using a single servo-control equation.

The kidney can also operate in hemodiafiltration mode in which the positions of the clamps and the operation of the pumps are the same as in hemodialysis mode, except that the pump 19 is controlled so as to give rise to ultrafiltration in the kidney in compliance with a given reference value for weight loss rate.

Figure 2:
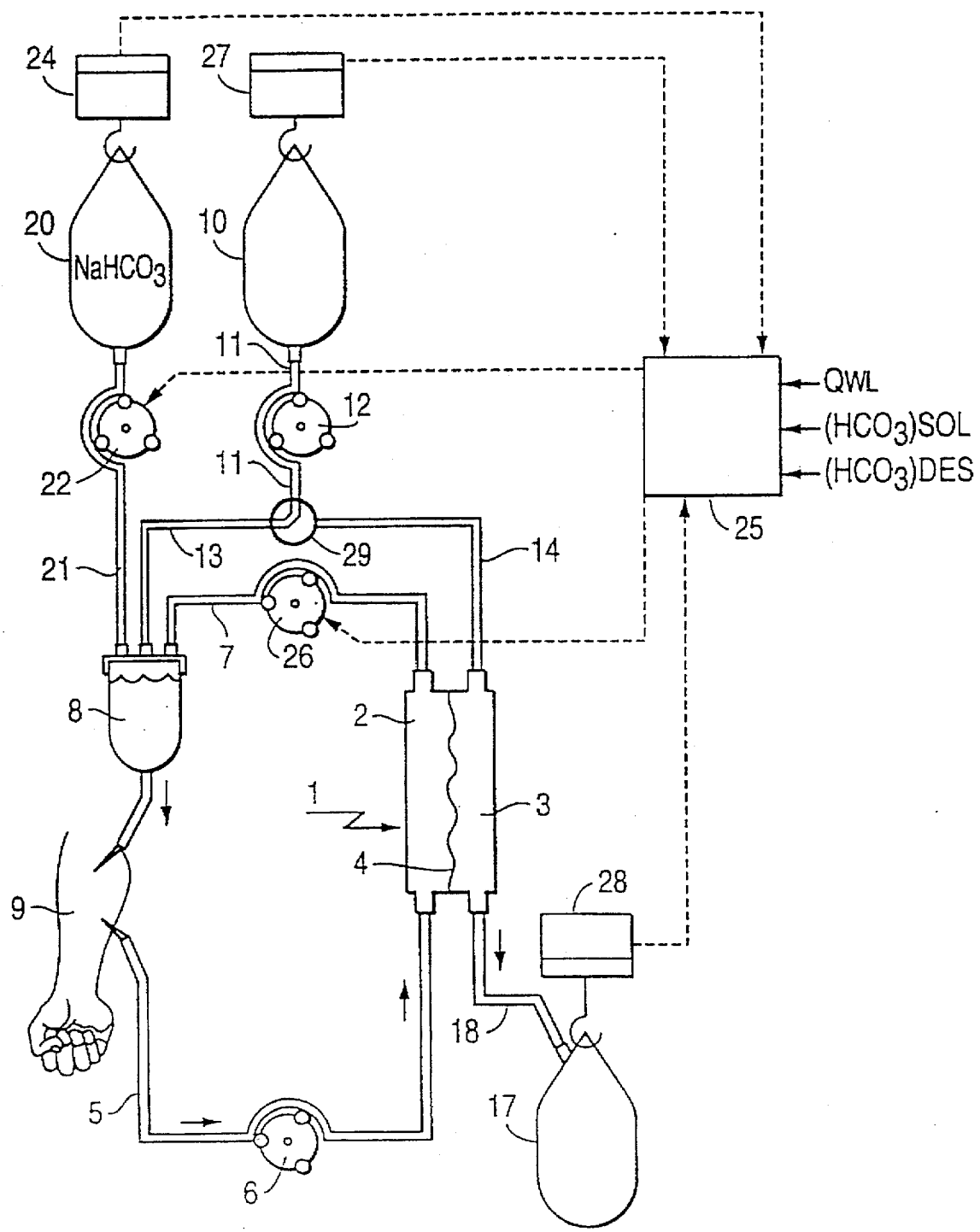
FIG. 2 is a simplified diagram of a second embodiment of the invention.

The artificial kidney shown in FIG. 2 differs from that described above in that its circuit for extracorporeal blood circulation includes a second pump 26 disposed downstream from the exchanger 1, thereby enabling the transmembrane pressure in the exchanger 1 to be varied and consequently enabling the flow rate of ultrafiltered plasma water to be varied (i.e. $Q_{OUT}$ in hemofiltration). In addition, the containers 10 and 17 for the substitution/dialysis and for the waste liquid are now weighed by independent scales 27, 28, and the duct 18 connecting the compartment 3 of the exchanger 1 to the waste liquid container 17 is not provided with a pump.

Moreover, a three-port valve 29 having the ducts 11, 13, and 14 connected thereto serves to connect the container 10 for the substitution/dialysis liquid either to the bubble trap 8 or to the compartment 3 of the exchanger 1, or else to isolate the container 10.

The operation of this second embodiment of the artificial kidney of the invention is not significantly different from that of the preceding embodiment. In hemofiltration mode without perfusion of substitution liquid, the pump 12 is off and the flow rate of the pump 26 is controlled by the control unit 25 so that the filtration flow rate $Q_{OUT}$ measured by the scales 28 is equal to the sum of the reference weight loss flow rate $Q_{WL}$ and the perfusion flow rate of bicarbonate solution $Q_{HCO3}$ as measured by the scales 24.

In hemofiltration mode with perfusion of substitution liquid, the pump 12 is on at a rate that is initially adjusted by the operator, and the rate of the pump 26 is controlled by the control unit 25 so that the filtration rate $Q_{OUT}$ is equal to the sum of the reference weight loss rate $Q_{WL}$, the perfusion rate of bicarbonate solution $Q_{HCO3}$, and the perfusion rate $Q_{IN}$ of substitution liquid as measured by the scales 27.

In dialysis mode, the pumps 6 and 26 on the blood circuit respectively upstream and downstream from the exchanger 1 operate at the same rate, and the pump 12 which then serves as a pump for circulating the dialysis liquid operates at a rate that is set initially by the operator.

In hemodiafiltration mode, the control unit 25 controls the flow rate of the pump 26 as in hemofiltration mode with perfusion of substitution liquid.

Except for hemofiltration mode in which it is off, the flow rate of the pump 12 for circulating the substitution/dialysis liquid is controlled by the control unit 25 which compares the desired flow rate stored initially in the memory of said unit with the flow rate as measured by the scales 27. The flow rate $Q_{HCO3}$ of the pump 22 for perfusing bicarbonate is controlled, as before, as a function of the waste liquid flow rate $Q_{OUT}$ as measured by the scales 24, in compliance with equation (1), or equation (2), as the case may be.

The invention is not limited to the embodiments described above and variants may be provided.

In particular, in contrast to the artificial kidney embodiments described above, in modes where the substitution/dialysis liquid is circulated by the pump 12, it is possible to have the flow rate of the pump 19 (26) that controls the ultrafiltration flow rate as the rate that is fixed initially by the operator, with the flow rate of the pump 12 being controlled as a function of the difference between the fresh liquids and the waste liquid as perfused and ultrafiltered, and the desired weight loss rate.

Moreover, the value of the liquid flow rates needed for controlling the pump 19 (26) controlling the ultrafiltration flow rate and for controlling the pump 22 for perfusing the bicarbonate solution could be determined by measurement means other than scales, for example using flow rate meters or volume-measuring means.

Moreover, the pumps 12 and 22 used for controlling the flow rate of substitution/dialysis liquid and the flow rate of bicarbonate solution could be replaced by electromagnetically-operated clamps, with the liquids then flowing under gravity.

Also the source 10 of perfusion liquid could be connected directly to the vascular system of the patient and not, as described before, to the circuit 5, 7 for extracorporeal blood circulation.

Finally, as mentioned above, the dosage means fitted to an artificial kidney of the invention may be used for dispensing all sorts of substances into the blood of a patient undergoing a treatment session by hemofiltration, hemodialysis, or hemodiafiltration. For a medicine A, for example, the container 20 would contain a sterile solution of the medicine with the container 10 containing a dialysis liquid in which the main electrolytes of blood are present, including bicarbonate. The operation of the kidney is no different from that described above with reference to the embodiments of FIGS. 1 and 2, and in particular, the perfusion pump 22 is controlled as a function of the flow rate of waste liquid in application of equation (1) or equation (2) as the case may be.

We claim:

1. An artificial kidney dosing method, comprising the steps of:
    connecting a patient to an exchanger having first and second compartments separated by a semipermeable membrane, the first compartment being connected to a circuit for extracorporeal blood circulation, and the second compartment having an outlet for draining a waste liquid;
    perfusing to the patient a perfusion liquid containing a substance (A);
    draining said waste liquid from said outlet; and
    adjusting the concentration of substance (A) in the blood of the patient to a desired concentration $\{A\}_{DES}$, by controlling a flow rate ($Q_A$) of the perfusion liquid as a function of (1) a flow rate ($Q_{OUT}$) of the waste liquid; (2) the desired concentration $\{A\}_{DES}$; and (3) a concentration $\{A\}_{SOL}$ of substance (A) in the perfusion liquid, whereby during the adjusting step a transfer of substance (A) through the semipermeable membrane is taken into account.

2. A dosing method according to claim 1, wherein the flow rate ($Q_A$) of the perfusion liquid the flow rate ($Q_{OUT}$) of the waste liquid are related by the equation:

$$Q_A = \frac{\{A\}_{DES}}{\{A\}_{SOL}} \times Q_{OUT}$$

where $\{A\}_{SOL}$ is the concentration of substance (A) in the perfusion liquid.

3. A dosing method according to claim 1, wherein the step of perfusing includes connecting a source of liquid through a canalization to the circuit for extracorporeal blood circulation.

4. A dosing method according to claim 3, wherein the flow rate of the perfusion liquid is varied using a pump disposed on the canalization connecting the source of perfusion liquid to the circuit for extracorporeal blood circulation.

5. A dosing method according to claim 1, wherein the flow rate of the perfusion liquid is controlled using a device for varying the flow rate of the perfusion liquid and a control unit for controlling the device.

6. A dosing method according to claim 5, wherein the device for varying the flow rate of the perfusion liquid is a pump disposed on the canalization connecting the source of perfusion liquid to the circuit for extracorporeal blood circulation.

7. A dosing method according to claim 1, wherein the substance (A) is bicarbonate.

8. A dosing method according to claim 7, further including the step of connecting a source of bicarbonate-free substitution liquid to the circuit for extracorporeal blood circulation.

9. A dosing method according to claim 7, further including the step of connecting a source of bicarbonate-free dialysis liquid to an inlet of the second compartment of the exchanger.

10. A dosing method according to claim 8, further including the steps of connecting a source of bicarbonate-free substitution/dialysis liquid to the circuit for extracorporeal blood circulation and to an inlet of the second compartment of the exchanger, and selectively isolating the source from the circuit.

11. A dosing method according to claim 1, further including the step of varying the ultrafiltration flow rate through the exchanger.

12. A dosing method according to claim 11, further including the step of controlling variance of the ultrafiltration flow rate as a function of the difference between liquids flow and a given reference value for weight loss flow rate ($Q_{WL}$).

13. A dosing method according to claim 1, further including the step of measuring a difference between perfusion liquid flow into the circuit and waste flow out of the second compartment of the exchanger.

14. A dosing method according to claim 13, wherein the step of measuring a difference of liquids flow is carried out using scales for weighing a difference between a container constituting a source of substitution/dialysis liquid and a container for collecting waste liquid, and scales for weighing a container constituting a source of solution containing the substance (A).

15. A dosing method according to claim 13, further including the step of controlling an ultrafiltration rate based on a comparison between a given value for weight loss flow rate ($Q_{WL}$), and a difference between liquid flow rate into the patient and the waste flow rate ($Q_{OUT}$).

16. A method for dosing a substance (A) in the blood of a patient, the method comprising the steps of:
    connecting the patient to an artificial kidney having an exchanger with two compartments separated by a semipermeable membrane, one of the compartments having an outlet for draining a waste liquid;
    perfusing into the patient a perfusion liquid containing the substance (A);
    draining waste liquid from the outlet; and
    controlling a flow rate ($Q_A$) of the perfusion liquid as a function of (1) a flow rate ($Q_{OUT}$) of the waste liquid; (2) a desired concentration $\{A\}_{DES}$ of substance (A) in the blood of the patient; and (3) a concentration $\{A\}_{SOL}$ of substance (A) in the perfusion liquid, whereby during the controlling step a transfer of substance (A) through the semipermeable membrane is taken into account.

17. A method according to claim 16, wherein the step of controlling includes regulating the flow rate ($Q_A$) of the perfusion liquid and the flow rate ($Q_{OUT}$) of the waste liquid in accordance with the following equation:

$$Q_A = \frac{\{A\}_{DES}}{\{A\}_{SOL}} \times Q_{OUT}$$

where $\{A\}_{SOL}$ is the concentration of substance (A) in the perfusion liquid.

18. An artificial kidney dosing method, comprising the steps of:

connecting a patient to an exchanger having first and second compartments separated by a semipermeable membrane, the first compartment being connected to a circuit for extracorporeal blood circulation, and the second compartment having an outlet for draining a waste liquid;

perfusing to the patient a perfusion liquid containing a substance (A);

draining said waste liquid from said outlet; and adjusting the concentration of substance (A) in the blood of the patient to a desired concentration $\{A\}_{DES}$ by controlling a flow rate ($Q_A$) of the perfusion liquid as a function of (1) a clearance Cl of the artificial kidney for the substance (A); (2) the desired concentration $\{A\}_{DES}$; and (3) a concentration $\{A\}_{SOL}$ of substance (A) in the perfusion liquid, whereby during the adjusting step a transfer of substance (A) through the semipermeable membrane is taken into account.

19. A dosing method according to claim 18, wherein the flow rate ($Q_A$) of the perfusion liquid and the clearance Cl of the artificial kidney for the substance (A) are related by the equation:

$$Q_A = \frac{\{A\}_{DES}}{\{A\}_{SOL}} \times Cl.$$

20. A method for dosing a substance (A) in the blood of a patient, the method comprising the steps of:

connecting the patient to an artificial kidney having an exchanger with two compartments separated by a semipermeable membrane, one of the compartments having an outlet for draining a waste liquid;

perfusing into the patient a liquid containing the substance (A);

draining waste liquid from the outlet; and adjusting the concentration of substance (A) in the blood of the patient to a desired concentration $\{A\}_{DES}$ by controlling a flow rate ($Q_A$) of the perfusion liquid as a function of (1) a clearance Cl of the artificial kidney for the substance (A); (2) the desired concentration $\{A\}_{DES}$; and (3) a concentration $\{A\}_{SOL}$ of substance (A) in the perfusion liquid, whereby during the adjusting step a transfer of substance (A) through the semipermeable membrane is taken into account.

21. A dosing method according to claim 20, wherein the flow rate ($Q_A$) of the perfusion liquid and the clearance Cl of the artificial kidney for the substance (A) are related by the equation:

$$Q_A = \frac{\{A\}_{DES}}{\{A\}_{SOL}} \times Cl.$$

* * * * *